United States Patent [19]

Ressemann

[11] Patent Number: 5,281,203
[45] Date of Patent: Jan. 25, 1994

[54] GUIDE WIRE AND SHEATH FOR SINGLE OPERATOR EXCHANGE

[75] Inventor: Thomas Ressemann, St. Cloud, Minn.

[73] Assignee: Scimed Life Systems, Inc., Maple Grove, Minn.

[21] Appl. No.: 725,064

[22] Filed: Jul. 5, 1991

[51] Int. Cl.⁵ ............................................. A61B 5/00
[52] U.S. Cl. ............................. 604/164; 604/280; 128/772
[58] Field of Search ............... 128/772, 657, 656, 658; 606/194; 604/95, 96, 158, 163, 164, 280, 165, 49, 52, 53

[56] References Cited

U.S. PATENT DOCUMENTS

| | | | |
|---|---|---|---|
| 4,425,919 | 1/1984 | Alston, Jr. et al. | 128/658 |
| 4,445,892 | 5/1984 | Hussein et al. | 604/101 |
| 4,748,984 | 6/1988 | Patel | 128/658 |
| 4,771,777 | 9/1988 | Horzewski et al. | 606/194 |
| 4,798,193 | 1/1989 | Giesy et al. | 128/7 |
| 4,817,613 | 4/1989 | Jaraczewski et al. | 128/658 |
| 4,846,193 | 7/1989 | Tremulis et al. | 128/772 |
| 4,898,577 | 2/1990 | Badger et al. | 604/53 |
| 4,928,693 | 5/1990 | Goodin et al. | 128/637 |
| 4,932,413 | 6/1990 | Shockey et al. | 128/657 |
| 4,967,753 | 11/1990 | Haase et al. | 128/662.06 |
| 4,976,720 | 12/1990 | Machold et al. | 606/194 |
| 4,986,814 | 1/1991 | Burney et al. | 604/164 |
| 4,988,356 | 1/1991 | Crittenden et al. | 606/192 |
| 4,994,027 | 2/1991 | Farrell | 604/53 |
| 5,007,901 | 4/1991 | Shields | 604/110 |
| 5,015,231 | 5/1991 | Keith et al. | 604/96 |
| 5,026,607 | 6/1991 | Kiezulas | 428/423.7 |
| 5,031,636 | 7/1991 | Gambale et al. | 128/772 |
| 5,046,497 | 9/1991 | Millar | 128/637 |
| 5,047,018 | 9/1991 | Gay et al. | 604/164 |
| 5,047,045 | 9/1991 | Arney et al. | 606/194 |
| 5,057,092 | 10/1991 | Webster, Jr. | 604/282 |
| 5,061,267 | 10/1991 | Zeiher | 606/40 |
| 5,066,285 | 12/1991 | Hillstead | 604/164 |
| 5,125,905 | 6/1992 | Wright et al. | 604/171 |

Primary Examiner—Stephen C. Pellegrino
Assistant Examiner—Guy V. Tucker
Attorney, Agent, or Firm—Willian Brinks Hofer Gilson & Lione

[57] ABSTRACT

A method and apparatus for exchanging a guide wire and for allowing blood perfusion through a body vessel in a procedure in which a guide wire is positioned in a body vessel with a proximal end of the guide wire extending out of the body and an intravascular device is positioned in the body vessel by passing a distal portion of the intravascular device over the guide wire while a proximal portion of the intravascular device is adjacent to the guide wire in the body vessel. A guide wire sheath is positioned over the guide wire so that a distal end of the sheath extends over the guide wire and into a lumen in the distal portion of the intravascular device. In another aspect, the guide wire can be withdrawn so that a distal end of the guide wire is located proximally of one or more openings in communicating with a lumen of the guide wire sheath so that blood can perfuse through the lumen of the guide wire sheath through the one or more openings and a distal opening communicating with the guide wire sheath lumen located distally of the one or more openings.

39 Claims, 1 Drawing Sheet

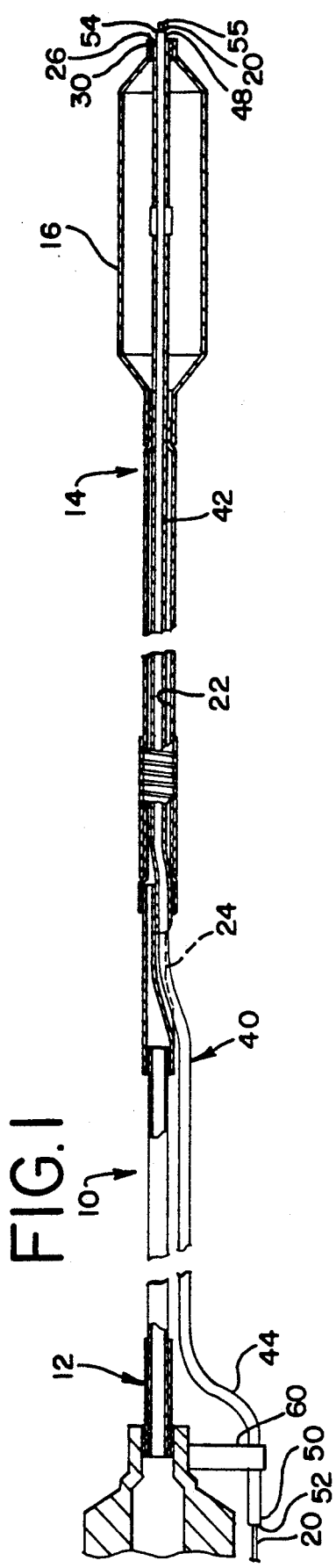
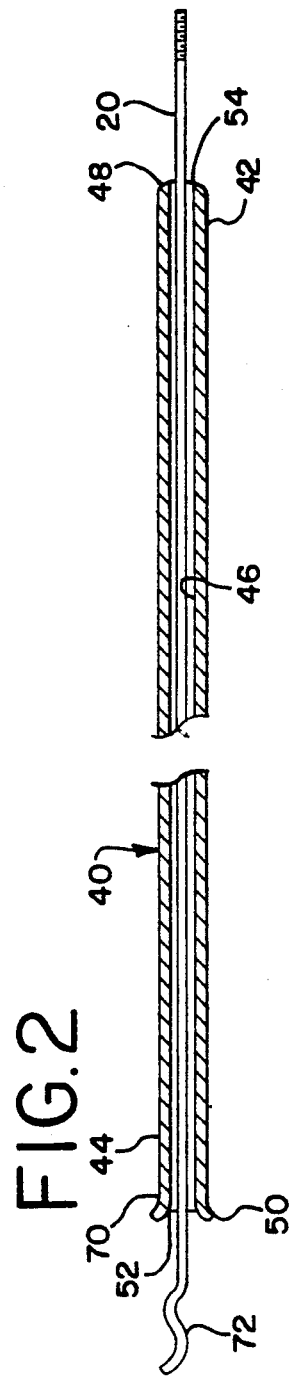
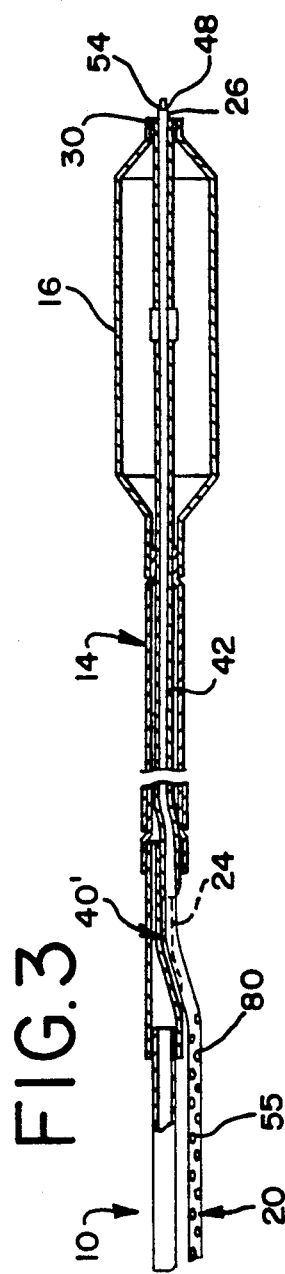

GUIDE WIRE AND SHEATH FOR SINGLE OPERATOR EXCHANGE

BACKGROUND OF THE INVENTION

This invention relates to methods and devices used in intravascular therapeutic and diagnostic procedures and in particular to methods and devices to facilitate a guide wire exchange in conjunction with another device used for intravascular therapies and diagnostics.

Intravascular therapeutic techniques, such as angioplasty, atherectomy, and laser irradiation, have been developed as alternatives to surgery for treating vascular disease or other conditions that occlude or reduce the lumen size of portions of a patient's vascular system. Also, intravascular diagnostic techniques, such as ultrasonic imaging, and Doppler blood flow measurements, have been developed to measure or image the extent of an occlusion of a vessel, (e.g., stenosis). These intravascular diagnostic techniques may be used in conjunction with the aforementioned therapeutic techniques or may be used in conjunction with more invasive techniques such as coronary surgery.

These intravascular therapeutic and diagnostic techniques have achieved acceptance because of their effectiveness as well as the fact that they can be performed through a minor surgical procedure that is relatively non-disruptive to the patient compared to coronary surgery. The intravascular therapeutic and diagnostic procedures, mentioned above, rely on the positioning of a device into the vascular system of a patient via an incision at an accessible location which may be remote from the site of the occlusion or stenosis. The accessible location may be for example the femoral artery. The intravascular device is then advanced through the incision via one or more vessels to the desired distal site. The vessels in the distal sites into which the device may be advanced include the coronary arteries, branch vessels stemming from the external carotid artery such as the occipital and the arteries leading to the vessels of the head and brain, splenic, and the inferior mesenteric and renal arteries leading to the organs of the thorax as well as other vessels. Because of the small size of some of these vessels and the tortuous passages through the vessels, positioning of a device through a patient's vasculature can be a difficult and time consuming task requiring considerable skill on the part of the physician.

Several different approaches have been developed for positioning intravascular therapeutic or diagnostic devices such as those mentioned above through a patient's vasculature. In one approach, a guide wire tip is fixed on a distal end of the intravascular device to facilitate maneuvering the device to the desired distally remote vessel site. Another approach uses an over-the-wire construction in which a central lumen of the intravascular device can accommodate a guide wire that is movable in relation to the device to facilitate positioning the device in a remote vessel location over the guide wire. In the over-the-wire construction, the intravascular device includes a lumen adapted to receive the guide wire from a proximal end to the distal end of the device. A guide wire would initially be loaded through the over-the-wire device from the proximal end thereof. Then, the guide wire and the intravascular device are positioned in the vessel to the desired site. The guide wire may be advanced distally of the distal end of the device, as necessary, to traverse tortuous passages of the vessel. The guide wire may then be withdrawn proximally through the lumen of the device or may be left in place extending from the distal end of the device during the procedure.

With both fixed wire and the over-the-wire devices, an introducer sheath and/or a guiding catheter may also be employed. An introducer sheath is used to provide translumenal access to the femoral artery or another appropriate location. Then, with the access provided by the introducer sheath, a guiding catheter may be positioned in the patient's vessel. The guiding catheter may be advanced at least part of the way to the desired site, such as to the aortic arch. The guiding catheter has an internal lumen through which the intravascular device, including the guide wire in an over-the-wire construction, is advanced. One of the functions of the guiding catheter is to support the device. The guiding catheter may be approximately 100 to 106 cm in length. Alternatively, in certain situation, e.g. if positioning of the device does not involve traversing tortuous vessel passages, a guiding catheter may be employed to position an intravascular device without the use of a guide wire.

Intravascular therapeutic and diagnostic devices, such as angioplasty and atherectomy devices, come in various types and sizes suitable for the vessel size and location in which the treatment is to be performed. Sometimes, it becomes necessary to exchange a first therapeutic device for one of a different size after the first device has been positioned or after an unsuccessful attempt to position the first device. This may be necessitated because it becomes apparent that the first device is the wrong size or because it is determined that additional therapeutic or diagnostic procedures with a different size or type of device is required.

When it is required to exchange one device for another, it a disadvantage of a fixed wire device that it is necessary to remove the entire device and position another device to the desired site. As mentioned above, this can be sometimes a tedious and difficult procedure.

In order to exchange an intravascular device with an over-the-wire construction, it may also be necessary to remove both the device and the guide wire. This is because it is preferred not to lose a hold on the proximal end of the guide wire as the device is withdrawn over the proximal end of the guide wire. Then, in order to position a second over-the-wire device, a guide wire must again be positioned to the desired location all over again in a new procedure just as was done for the first device. This can be timeconsuming and thus requires the physician to perform again the sometimes difficult and tedious task of positioning the guide wire to the desired location. Replacement of both the device and the guide wire may also be necessary when the second device is to be advanced to a different vessel site requiring a guide wire of a different size or of different dimensions.

It is possible in some situations to exchange the intravascular device and leave the guide wire in place. This can greatly facilitate exchanging the device because the difficult task of positioning the guide wire need not be performed again. An intravascular device with an over-the-wire construction can be exchanged while leaving the distal tip of the guide wire in place according to several different methods. For example, one method is to use a guide wire having a long length (e.g. 300 cm) so that a sufficiently long proximal portion of the guide wire extends out of the proximal end of the guiding catheter in order that the entire intravascular device can be withdrawn out completely over the guide wire while maintaining a hold on a proximal portion of the guide wire. This method has the disadvantage that the long proximally extending portion of the long guide wire may be in the way during the procedure. Another method to exchange an intravascular device with an over-the-wire construction is by using a guide wire extension. A description of this method is in "Guide Wire Extension", by C. Cope, M.D., *Radiology* 1985; 157:263 (1985). A disadvantage of this method is that not all guide wires are adapted to connect to an extension wire, and moreover, the step of connecting the guide wire to the extension wire can sometimes be tedious and difficult to do.

One approach that is employed to facilitate exchange of intravascular devices is the "single-operator-exchange" construction. With the single-operator-exchange construction, a guide wire occupies a position adjacent to the intravascular device along proximal and middle portions of the device and enters into a lumen of the device via a laterally-oriented opening at a location close to a distal portion of the device. With this construction, the device can be positioned in the patient's vessel by positioning a guide wire in the desired location and advancing the device over the wire. However, in the event that it becomes necessary to exchange the single-operator-exchange device, the device can be withdrawn proximally while the distal tip of the guide wire is left in position in the vessel site. Because the proximal end of the guide wire and the proximal end of the device are adjacent to each other, the proximal end of the guide wire can be secured so that the position of the distal end of the guide wire in the patient's vessel can be maintained. With this type of device, it is necessary that the distance from the distal end of the device to the lateral proximal guide wire entrance is less than the proximal length of the guide wire that extends out of the guiding catheter.

Just as it sometimes becomes necessary to exchange the device, it also sometimes becomes necessary to exchange the guide wire. A guide wire exchange may be necessary for example when it is determined after the guide wire and the device are in the vessel that the guide wire must be advanced further and a guide wire of a different size or construction or with a different tip "bend" is necessary. With a device with an over-the-wire construction, the guide wire can be withdrawn through the lumen of the device and a second guide wire installed while leaving the device in position. However, with the single-operator-exchange construction, a guide wire exchange cannot readily be performed without withdrawing the device because once the distal end of the first guide wire is withdrawn proximally from the proximal guide wire lumen opening of the device, a second guide wire cannot readily be positioned in the proximal guide wire lumen opening without also withdrawing the device proximally at least so that the proximal guide wire lumen opening is outside the guiding catheter.

Accordingly, it is an object of the present invention to provide a method and device to facilitate a guide wire exchange in conjunction with intravascular devices that incorporate a single-operator-exchange construction.

SUMMARY OF THE INVENTION

The present invention relates to a method and apparatus for exchanging a guide wire and for allowing blood perfusion through a body vessel in a procedure in which a guide wire is positioned in a body vessel with a proximal end of the guide wire extending out of the body vessel and an intravascular device is positioned in the body vessel by passing a distal portion of the intravascular device over the guide wire while a proximal portion of the intravascular device is adjacent to the guide wire in the body vessel. A guide wire sheath is positioned over the guide wire so that a distal end of the sheath extends over the guide wire and into a lumen in the distal portion of the intravascular device.

In another aspect, the guide wire can be withdrawn so that a distal end of the guide wire is located proximally of one or more openings in communicating with a lumen of the guide wire sheath so that blood can perfuse through the lumen of the guide wire sheath through the one or more openings and a distal opening communicating with the guide wire sheath lumen located distally of the one or more openings.

BRIEF DESCRIPTION OF THE FIGURES

FIG. 1 depicts a first preferred embodiment of the present invention.

FIG. 2 shows a longitudinal sectional view of an embodiment of the guide wire sheath depicted in FIG. 3 shows another embodiment of the guide wire sheath depicted in FIG. 1.

DETAILED DESCRIPTION OF THE PRESENTLY PREFERRED EMBODIMENTS

With reference to FIG. 1, a first embodiment of the present invention shall be described. In this embodiment, a single-operator-exchange type device 10 is depicted. In this embodiment, the single-operator-exchange 10 is an Express ® balloon catheter made by Scimed Life Systems, Inc. of Maple Grove, Minn. The Express ® balloon catheter is used to perform an angioplasty procedure. Alternatively, other therapeutic or diagnostic devices that can be positioned in a body vessel and that have a laterally-oriented opening to a distally extending lumen for receiving a guide wire may be used. Such devices may include, but are not limited to, atherectomy devices, laser irridation devices, imagers, Doppler monitors, etc.

The single-operator-exchange device 10 includes a proximal portion 12 which extends outside of the body of the patient and a distal portion 14. An inflatable balloon 16 is located on the distal portion 14. Appropriate connections are provided on the proximal portion 12 to inflate and deflate the balloon 16 to dilate a vessel in manner that is well known in the art.

Positioning of the single-operator-exchange device 10 is facilitated by means of a guide wire 20. The guide wire 20 is positioned in a lumen 22 of the single-operator-exchange device 10. The lumen 22 has a proximal opening 24 for receiving the guide wire 20 and a distal opening 26. In the Express ®, the proximal opening 24 is located approximately 35 cm from a distal end 30 of the single-operator-exchange device 10. The proximal opening 24 opens laterally so that the guide wire 20 is positioned adjacent to the device 10 proximally from the proximal opening 24. The distal opening 26 is located at the distal end 30 of the device. The lumen 22 extends from the proximal opening 24 to the distal opening 26.

According to the present embodiment, a guide wire sheath 40 is provided. The guide wire sheath 40 includes a distal portion 42 and a proximal portion 44. A sheath lumen 46 extends from a distal end 48 of the guide wire sheath 40 to a proximal end 50 of the guide wire sheath 40. A proximal sheath opening 52 and a distal sheath opening 54 communicate with the sheath lumen 46.

According to this embodiment, at least a portion of the guide wire sheath 40 is positioned in the device 10 in the device lumen 22. Preferably, a distal portion 42 of the guide wire sheath 40 is located in the lumen 22 of the single-operator-exchange device 10. A distal end 55 of the guide wire 20 may be extended past the distal end 48 of the guide wire sheath 40 and past the distal end 30 of the single-operator-exchange device 10 to facilitate positioning of the single-operator-exchange device 10 in a patient's vessel.

Use of the guide wire 20 to position the single-operator-exchange device 10 may be performed in a manner as had been done with the Express ® without use of the guide wire sheath 40. In addition, exchange of the single-operator-exchange device 10 can also be performed. In performing an exchange of a first single-operator-exchange device with another single-operator-exchange device when using a guide wire sheath, the first device is withdrawn proximally while both the guide wire and the guide wire sheath remain in place in the patient's vessel.

According to the present embodiment, exchange of the guide wire 20 may be provided with the single-operator-exchange device 10 without removal of the single-operator-exchange device. As mentioned above, it may be necessary to exchange the guide wire after the guide wire and single-operator-exchange device have been positioned in the patient's vessel. According to this embodiment, a guide wire exchange may be performed by withdrawing the guide wire 20 proximally through the guide wire sheath 40 while maintaining the distal end 42 of the guide wire sheath 40 distal of the proximal opening 24 of the single-operator-exchange device 10. The proximal end 44 of the guide wire sheath 40 may be maintained fixed to prevent its movement relative to the single-operator-exchange device 10. A connecting member 60 between the proximal end of the guide wire sheath 40 and a proximally located manifold 62 of the single-operator-exchange device 10 may be provided to fix the proximal ends of the single-operator-exchange device 10 and the guide wire sheath 40 to prevent relative movement. The connecting member 60 may be a clamp or other such device.

Once the guide wire 20 is completely withdrawn from the proximal end 50 of the guide wire sheath 40, a second guide wire may be advanced through the guide wire sheath 40 out the distal ends 48 and 30 of the guide wire sheath 40 and the single-operator-exchange device 10. The second guide wire may be of a different size or have different characteristics or properties than the first guide wire, such as being more flexible or having a particular bend, and may be more suitable for locating the device.

According to this embodiment, the distal end 48 of the guide wire sheath 40 may be located distally of the distal end 30 of the single-operator-exchange device 10. Alternatively, the distal end 48 of the guide wire sheath 40 may be located proximally of the distal end 30 of the single-operator-exchange device 10 inside of the device lumen 22.

In positioning the device in the patient's vessel, a guiding catheter (not shown) may also be employed in a manner that is well known in the art. When used with the above described embodiment of the present invention, a guiding catheter should have a lumen of a size sufficient to accommodate the device, the guide wire, and the guide wire sheath.

The guide wire sheath 40 may be positioned in the device 10 while at least the proximal opening 24 of the device 10 is outside of the patient. Preferably, the guide wire sheath 40 is positioned in the device lumen 22 while the device 10 is entirely outside of the patient. The guide wire sheath 40 should be placed over the guide wire 20 prior to advancing the guide wire to the desired site. A guiding catheter (not shown) may be employed to accommodate advancing the device, the guide wire and the guide wire sheath. The device 10 is then advanced in the same manner as has been done previously.

Referring to FIG. 2, a portion of an embodiment of the guide wire sheath is depicted. In this embodiment, a wire clutching mechanism 70 is provided. The wire clutching mechanism 70 is located near the proximal end 50 of the sheath. The wire clutching mechanism comprises a crimp in the body of the sheath to provide a tight fit between the sheath and the guide wire. This clutching mechanism reduces or prevents unintentional relative movement between the sheath and the guide wire. The clutching mechanism may be provided by other means such as by a clamping device.

Also as shown in FIG. 2, the guide wire 20 may be provided with a restraining means 72 on a proximal end thereof to reduce the possibility that the proximal end of the guide wire might slide distally of the proximal opening 52 of the guide wire sheath. The retaining means 72 may be a bend or crimp in the proximal portion of the guide wire or may be provided by other means such as by a hypotube.

The guide wire sheath should be provided in a length sufficient so that a distal end can be positioned in the guide wire lumen of the single-operator-exchange device while a proximal end of sheath extends outside of the guiding catheter. Also, the guide wire sheath should be provided in a length short enough so that the guide wire extends proximally from the proximal end of the guide wire sheath when the guide wire is positioned in the sheath and out of the distal end of the device. Thus, it may be that the guide wire sheath is provided in various lengths to be suitable for different devices. For use with an Express ® catheter, a guide wire sheath having a length of 160–165 cm is preferred.

In a preferred embodiment, the guide wire sheath is made of a polymeric material, such as polyimide, and has a Teflon ® coating on at least one surface thereof. In a preferred embodiment, the guide wire sheath has a Teflon ® coating on both the inner and outer surfaces thereof. Alternatively, the guide wire sheath may be made of other materials, such as polyurethane, polyester, or other polymers. The guide wire sheath may also be made of a polyimide-teflon composite material. The guide wire sheath may be reinforced with wire or a braid 73 of metal or plastic or other materials. Also alternatively, the coating may be of other materials such as a hydrophilic coating or a coating of silicone or other lubricious material. A coating on the inner surface enhances guide wire movement through the guide wire sheath and a coating on the outer surface enhances sheath movement through the vessel, a guiding catheter or the device lumen. In addition to or instead of the lubricious coating, a metallic or foil coating may also be incorporated on at least one surface of the guide wire sheath.

The guide wire sheath may be provided in different sizes to be suitable for different size devices. For example, the guide wire sheath may be provided with an inner diameter of 0.015 inches and an outer diameter of 0.0165 inches for use with a 0.014 inch guide wire. For use with a 0.010 inch guide wire, the guide wire sheath may be provided with an inner diameter of 0.011 and an outer diameter of 0.0125. The guide wire sheath can be provided in other sizes as well.

FIG. 3 illustrates a portion of another embodiment of the invention incorporating a guide wire sheath 40'. This embodiment incorporates features adapted to provide for blood perfusion when used with a single-operator-exchange device of the type described above. In an angioplasty procedure, it is sometimes a concern that the balloon obstructs the blood flow through the artery during the period of time when the balloon is inflated. With the embodiment of the sheath 40' shown in FIG. 3, this concern is addressed.

The guide wire sheath 40' may be provided in the same or similar dimensions and may be provided in the same or similar materials and may have the same or similar construction as the guide wire sheath 40, described above and depicted in FIGS. 1 and 2. Moreover, the guide wire sheath 40' of FIG. 3 may be used in the same or similar manner as the guide wire sheath 40 described and depicted in FIGS. 1 and 2, i.e. to provide the ability to exchange guide wires with a single-operator-exchange device.

The guide wire sheath 40' includes one or more perfusion openings 80. The perfusion openings 80 are located in a portion of the sheath 40' which is located proximally of the opening 24 of the device 10 (and thereby adjacent to the device) when the guide wire sheath 40' is positioned in the intravascular device 10 with a distal end 48 of the sheath 40' in the lumen 22 of the intravascular device 10 distal of the opening 24. The perfusion openings 80 allow blood to perfuse via the portion of the lumen 46 of the guide wire sheath 40' between the openings 80 and the distal opening 54 of the guide wire sheath 40'. This provides for perfusion past the balloon portion of the intravascular device 10 thereby reducing the possibility of complications due to obstructing blood flow past the balloon.

In a preferred embodiment, the perfusion openings 80 are located at least in a portion of the sheath 40' that extends from the proximal end 50 of the sheath 40' to a location approximately 35 cm proximal of the distal end 48 of the sheath 40'. Thus, the perfusion openings 80 would extend over the entire portion of the sheath 40' proximal of the location 24 at which the sheath 40 enters the device lumen 22 thus affording a substantial area through which blood can perfuse. The perfusion openings 80 may be each approximately 0.010 to 0.012 inches in diameter. The perfusion openings may be located in the wall of the sheath at intervals from each other of approximately ¼ inch. Also, the perfusion openings may be staggered so that adjacent openings on the same side of the sheath are separated by approximately ¼ inch to maintain the structural integrity of the sheath.

In accordance with this embodiment, the intravascular device 10 is positioned with the guide wire sheath 40' in accordance with the method described above. The guide wire sheath 40' is positioned so that the openings 80 are proximal of the opening 24 of the intravascular device 10. After the balloon 16 is positioned in the desired location, the guide wire 20 is withdrawn proximally so that the distal end 55 of the guide wire 20 is proximal of the openings 80 (as shown by the dashed lines in FIG. 3). The balloon 16 may be then inflated and used in the manner as is well known in the art. Blood may perfuse through the intravascular device 10 via the openings 80 and the distal opening 54 of the sheath 40' even when the balloon is inflated. Thus, this embodiment of the invention provides the advantage that the vessel is not completely obstructed when the balloon is inflated and therefore the balloon may be deployed for a greater duration of time. If it is desired to reposition the intravascular device 10, the guide wire 20 is readily advanced distally in the guide wire sheath 40' past the distal end of the intravascular device 10 for that purpose. This embodiment may be employed with intravascular devices other than balloon catheters where a concern exists about allowing blood perfusion past the intravascular device.

It is intended that the foregoing detailed description be regarded as illustrative rather than limiting and that it is understood that the following claims including all equivalents are intended to define the scope of the invention.

I claim:

1. A method for exchanging a guide wire comprising:
    positioning a guide wire in a body vessel with a proximal end of the guide wire extending out of the body vessel;
    positioning an intravascular device in the body vessel by passing a distal portion of the intravascular device over the guide wire through a distal guide wire lumen of the intravascular device, the intravascular device being of a type in which the distal guide wire lumen has a proximal guide wire lumen opening through a side wall of the intravascular device so that a proximal portion of the intravascular device is adjacent to the guide wire proximal of said proximal guide wire lumen opening,
    positioning a sheath over the guide wire; and
    advancing the sheath so that a distal end of the sheath extends over the guide wire and advancing the sheath over the guide wire or into the guide wire lumen opening of the intravascular device;
    withdrawing the guide wire from the sheath for exchange.

2. The method of claim 1 wherein a step of withdrawing includes:
    withdrawing the guide wire from the intravascular device through the sheath while the distal end of the sheath remains in the intravascular device.

3. The method of claim 2 further comprising the step of:
    positioning a second guide wire in the intravascular device by advancing said second guide wire through the sheath and into the intravascular device while the intravascular device is positioned in the vessel.

4. The method of claim 1 in which the sheath positioning step further comprises:
    positioning the sheath over the guide wire so that the distal end of the sheath extends out a distal opening of the lumen of the intravascular device.

5. The method of claim 1 in which the step of positioning a sheath is performed before the step of positioning an intravascular device.

6. The method of claim 1 further comprising the step of:

withdrawing the guide wire proximally in the sheath so that a distal end of the guide wire is located proximally of one or more openings in a wall of the sheath in a portion thereof located adjacent said intravascular device that communicate with a sheath lumen that extends distally and that opens to the distal end of the sheath, whereby blood can perfuse through the sheath lumen.

7. A method for providing blood perfusion through at least a portion of an intravascular device comprising:
   positioning a guide wire in a body vessel with a proximal end of the guide wire extending out of the body vessel;
   positioning an intravascular device in the body vessel by passing a distal portion of the intravascular device over the guide wire through a distal guide wire lumen of the intravascular device, the intravascular device being of a type in which the distal guide wire lumen has a proximal guide wire lumen opening through a side wall of the intravascular device so that a proximal portion of the intravascular device proximal of the proximal guide wire lumen opening is adjacent to the guide wire;
   positioning a sheath over the guide wire so that a distal end of the sheath extends over the guide wire and into the proximal guide wire lumen opening of the intravascular device; and
   withdrawing the guide wire proximally in the sheath so that a distal end of the guide wire is located proximally of one or more openings in a wall of the sheath that communicate with a sheath lumen that extends distally and that opens to the distal end of the sheath, whereby blood can perfuse through the sheath lumen.

8. In combination,
   an intravascular device insertable into a body vessel with a guide wire lumen in a distal portion thereof with a proximal guide wire lumen opening communicating with the guide wire lumen, and further in which the proximal guide wire lumen opening is located through a side wall of the intravascular device substantially distal of the proximal end of the intravascular device;
   a sheath having:
      a distal end removably positioned in the guide wire lumen opening of the intravascular device,
      the sheath further having a length with respect to the intravascular device such that a proximal end of said sheath is positionable outside the body vessel when said distal end is positioned in said guide wire lumen opening during use of the intravascular device, and
      a sheath lumen through the distal and proximal ends of the sheath; and
   a guide wire removably locatable in said sheath.

9. The invention of claim 8 further comprising:
   a coating on at least one surface of said sheath.

10. The invention of claim 9 in which said coating is on an inner surface of said sheath.

11. The invention of claim 9 in which said coating is on an outer surface of said sheath.

12. The invention of claim 9 in which said coating is a polytetrafluoroethylene coating.

13. The invention of claim 8 further comprising a connecting member for connecting the proximal end of the sheath to a proximal end of the intravascular device.

14. The invention of claim 8 further comprising a wire clutching means associated with the sheath to secure the guide wire therein.

15. The invention of claim 14 in which said wire clutching means further comprises:
   a crimp located in the proximal end of the sheath.

16. The invention of claim 8 in which said sheath is made of polyimide.

17. The invention of claim 8 in which said sheath is made of polyimide with a polytetrafluoroethylene coating.

18. The invention of claim 8 in which said sheath is made of composite material comprised of polyimide and polytetrafluoroethylene.

19. The invention of claim 8 in which said sheath includes a reinforcing braid.

20. The invention of claim 8 in which said sheath is comprised of a polymeric material with a coating located thereon selected from a group consisting of: a metallic coating and a foil coating.

21. The invention of claim 8 in which said sheath is made of a polymeric material.

22. The invention of claim 8 in which said sheath lumen has a distal opening and one or more openings located proximal of the distal opening in a portion locatable proximal of the proximal lumen opening of the intravascular device, whereby blood can perfuse through the sheath lumen when the guide wire is withdrawn proximally of the one or more openings.

23. In combination
   an intravascular device of a type wherein the intravascular device has a guide wire lumen in a distal portion thereof with a proximal guide wire lumen opening communicating with the guide wire lumen, and further in which the proximal guide wire lumen opening is located through a side wall of the intravascular device substantially distal of a proximal end of the intravascular device;
   a sheath having:
      a distal end removably positioned in the guide wire lumen opening of the intravascular device,
      the sheath further having a length with respect to the intravascular device such that a proximal end of said sheath is positionable outside the body vessel when said distal end is positioned in said guide wire lumen opening during use of the intravascular device, and
      a sheath lumen through the distal and proximal ends of the sheath, the sheath lumen having a proximal sheath lumen opening communicating therewith, a distal sheath lumen opening, and one or more openings located proximal of the distal sheath lumen opening; and
   a guide wire removably positioned inside said sheath lumen, whereby blood can perfuse through the sheath lumen of the sheath.

24. The invention of claim 23 further comprising:
   a coating on at least one surface of said sheath.

25. The invention of claim 24 in which said coating is on an inner surface of said sheath.

26. The invention of claim 24 in which said coating is on an outer surface of said sheath.

27. The invention of claim 24 in which said coating is a polytetrafluoroethylene coating.

28. The invention of claim 23 further comprising a connecting member for connecting the proximal end of the sheath to a proximal end of the intravascular device.

29. The invention of claim 23 further comprising a wire clutching means associated with the sheath to secure the guide wire therein.

30. The invention of claim 29 in which said wire clutching means further comprises:
a crimp located in the proximal end of the sheath.

31. The invention of claim 23 in which said sheath is made of polyimide.

32. The invention of claim 23 in which said sheath is made of polyimide with a polytetrafluoroethylene coating.

33. The invention of claim 23 in which said sheath is made of composite material comprised of polyimide and polytetrafluoroethylene.

34. The invention of claim 23 in which said sheath includes a reinforcing braid.

35. The invention of claim 23 in which said sheath is made of a polymeric material.

36. The invention of claim 23 in which said sheath is comprised of a polymeric material with a coating located thereon selected from a group consisting of: a metallic coating and a foil coating.

37. The invention of claim 23 in which the one or more openings in said sheath located proximal of the distal opening are of a size on the order of approximately 0.010 to 0.012 inches.

38. The invention of claim 23 in which the openings in said sheath located proximal of the distal opening are spaced from each other by approximately 150 inches.

39. The invention of claim 23 in which the openings in said sheath located proximal of the distal opening are staggered from each other.

* * * * *